US00RE39337E

(19) United States
(12) Reissued Patent
Monosov et al.

(10) Patent Number: US RE39,337 E
(45) Date of Reissued Patent: Oct. 10, 2006

(54) NUDE MOUSE MODEL FOR HUMAN NEOPLASTIC DISEASE

(75) Inventors: Ann Monosov, Encinitas, CA (US); Xinyu Fu, Providence, RI (US)

(73) Assignee: Anticancer, Inc., San Diego, CA (US)

(21) Appl. No.: 09/023,232

(22) Filed: Feb. 13, 1998

Related U.S. Patent Documents

Reissue of:
(64) Patent No.: 5,569,812
Issued: Oct. 29, 1996
Appl. No.: 08/459,730
Filed: Jun. 2, 1995

U.S. Applications:
(63) Continuation of application No. 08/169,735, filed on Dec. 17, 1993, now Pat. No. 5,491,284, which is a continuation of application No. 07/719,814, filed on Jun. 24, 1991, now abandoned, which is a continuation-in-part of application No. 07/253,990, filed on Oct. 5, 1988, now abandoned.

(51) Int. Cl.

| | |
|---|---|
| ***A01K 67/00*** | (2006.01) |
| ***A61K 35/12*** | (2006.01) |
| ***A61K 35/36*** | (2006.01) |
| ***A61K 35/42*** | (2006.01) |
| ***A61K 49/00*** | (2006.01) |

(52) U.S. Cl. ..... 800/8; 800/9; 424/9.2; 424/573; 424/559; 424/557; 424/574

(58) Field of Classification Search ..... 800/9, 800/10; 424/93.21
See application file for complete search history.

(56) References Cited

U.S. PATENT DOCUMENTS 5,491,284 A * 2/1996 Monosov et al. ..... 800/10

OTHER PUBLICATIONS

Wang et al. (1982) Exp. Cell. Biol., vol. 50, 330–331.*
McLemore et al. (1987) Cancer Res., vol. 47 (19), 5132–5140.*
Otto et al. (1985) J. Urol., vol. 134, 170–174.*
Reddy et al. (1987) Cancer Res., vol. 47 (9), 2456–2460.*
Giovanella et al. (1984) Exp. Cell. Biol., vol. 52, 76–79.*
Shapiro et al., J. Natl. Cancer Inst. (1979) 62:447–453.
Fidler, Cancer and Metastasis Reviews (1986) 5:29–49.
Naito et al., Cancer Research (1986) 46:4109–4115.
Kyriazis et al., Cancer Research (1981) 41:3995–4000.
Morikawa et al., Cancer Research (1988) 48:1943–1948.
Furukawa et al., Cancer Research (1993) 53:1204–1208.
An et al., Clinical and Experimental Metastasis (in press) (1999).
Fu et al., Int. J. Cancer (1991) 49:938–939.
Fu and Hoffman, Int. J. Cancer (1992) 51:989–991.
Detry et al., Transplantation (2000) 70:244–248.
Widjaja et al., Digestion (2000) 61:219–222.
Lopez–Rios et al., Diagnostic Cytopathology (2000) 23:43–45.
Interlocutory decision in Opposition proceedings (Articles 102(3) and 106(3) EPC) (Dec. 4, 2000).

* cited by examiner

*Primary Examiner*—Q. Janice Li
(74) *Attorney, Agent, or Firm*—Morrison & Foerster LLP

(57) ABSTRACT

A nude mouse model for human neoplastic diseases having histologically intact human neoplastic tissue transplanted onto an organ of the mouse which corresponds to the human organ from which the tissue is obtained.

50 Claims, No Drawings

NUDE MOUSE MODEL FOR HUMAN NEOPLASTIC DISEASE

Matter enclosed in heavy brackets [ ] appears in the original patent but forms no part of this reissue specification; matter printed in italics indicates the additions made by reissue.

RELATED APPLICATIONS

This application is a continuation of U.S. Ser. No. 08/169,735, filed Dec. 17, 1993, now U.S. Pat. No. 5,491,284, which is a continuation of U.S. Ser. No. 07/719,814 filed Jun. 24, 1991, now abandoned, which is a continuation-in-part of U.S. Ser. No. 253,990 filed Oct. 5, 1988, now abandoned, the contents of which are hereby incorporated by reference in their entirety.

TECHNICAL FIELD

The present invention relates generally to a non-human mammalian model for human neoplastic diseases. More particularly, the invention relates to a non-human mammalian model having neoplastic tissue, obtained from a human organ, transplanted to the corresponding organ of the model.

BACKGROUND

There has long been a need for a representative animal model for human neoplastic disease. Such a model could serve many purposes. For example, it would be used to study the progression of neoplastic disease in human subjects and assist in finding appropriate treatment. Such a model could also be used to test the efficacy of proposed anti-neoplastic agents. Additionally, an animal model could be employed in individualized chemosensitivity testing of a cancer patient's tumors. The existence of such a model would make drug screening, testing and evaluation much more efficient and much less costly.

Some previous attempts at generating animal models for human neoplastic disease employed transplantable animal tumors. There were tumors that had developed in rodents and had been transplanted from animal to animal, usually in inbred populations. Other animal tumor models were generated by inducing tumors in the animals by means of various agents that were carcinogenic, at least in the animal system. Still other animal tumor models were rodents containing spontaneously-occurring tumors. These rodent models, however, frequently responded to chemotherapeutic agents very differently than human subjects receiving the same agent.

Another animal tumor model that developed starting some twenty years ago utilized mice without a thymus gland. These animals were deficient in cellular immunity and had therefore lost their ability to reject foreign transplant tissue. The mice, for reasons not clearly understood, were essentially lacking in hair and came to be called "nude mice" or "athymic T-cell deficient nude mice."

It was found that human tumors often grew when implanted subcutaneously under the skin of nude mice, however, the take rate or frequency with which human tumor tissue actually formed a tumor in the mouse varied depending on the individual donor and the tumor type. In these models, tumors that took exhibited histologically limited invasiveness and rarely metastasized, even if the original human tumor had been highly metastatic. Accordingly, the subcutaneous nude mouse human tumor model, although better than the previously described rodent model, still had substantial drawbacks, i.e. the subcutaneous transplants lacked the ability to metastasize, and also were often more sensitive than the tumor in the patient in the original organ. The differences may be due to the subcutaneous environment regarding pH, vascularity, accessibility to drugs, etc.

Subsequent investigators found that invasion and metastases by human tumor cells in nude mice appeared to require that the cells be implanted orthotopically, i.e. injected into organs involved in the original anatomical environment of the tumor. For example, Wang et al. (Exp. Cell Biology, 50, 330 (1982)) report the expression of malignant phenotype when human colonic tumor cells were implanted by injection within the colonic wall of nude mice. Moreover, Natio et al. (Cancer Research, 46, 4109 (1986)) and Naito et al. (JNCI, 78,377 (1987)) report growth and metastasis of tumor cells isolated from a human renal cell carcinoma and implanted by injection into the kidneys of nude mice. More recently, Morikawa et al. (Cancer Research, 46, 6863 (1988) report the growth of human colon carcinoma cells implanted by injection within the spleens of nude mice.

While the human tumor model created by orthotopic implantation of human tumor cells in the nude mouse represents a significant advance over earlier models, the value of this model is clearly dependent on the extent to which the character of the original human tumor is maintained in the immunodeficient host. Human tumor cells utilized in orthotopic implantation are derived from tumor tissue that is disassociated enzymatically. Enzymatic disassociation disrupts the architecture of the tumor tissue and thus the unique cellular organization. Cells behave very differently when they are organized in a tissue structure as opposed to being disassociated.

Neoplasms are biologically heterogeneous, consisting of different subpopulations of cells having different biological behavior and different metastatic potential (see Naito et al., Cancer Research, 46, 4109–4115 (1986); Naito et al., JNCI, 78,377 (1987); and Morikawa et al., Cancer Research, 48, 6863 {1988}). Enzymatic disassociation of tumor tissue, the conventional method used to isolate tumor cells from fresh surgical specimen, disrupts the original tumor architecture and precludes obtaining a truly representative tumor cell population for implantation. Enzymatic disassociation also alters cellular behavior and drug response.

For example, in routine location of tumor cells for implantation or sensitivity testing, tumor tissue from a surgical specimen is disassociated enzymatically to produce cells which are then implanted subcutaneously (s.c.) in nude mice. The purpose of the s.c. implant is to produce a larger amount of tumor tissue for studies of predictive sensitivity for therapeutic agents as well as for implantation. After sufficient s.c. tumor growth occurs, the tumor is excised and disassociated enzymatically. As mentioned previously, enzymatic disassociation of the tumor cells disrupts the tumor architecture and consequently cells that are selected for sensitivity testing or orthopedic implantation by injection may not be representative or characteristic of the original patient tumor.

Thus the art is presently lacking a truly adequate non-human mammalian model for human neoplastic disease. In particular, what is needed in the art is a model which has the ability to accurately mimic the progression of neoplastic disease as it occurs in a human subject. Such models and methods of generating same are disclosed and claimed herein.

SUMMARY AND OBJECTS OF THE INVENTION

The present invention relates to an improved non-human mammalian model for human neoplastic disease.

In a first aspect, the present invention provides a novel non-human mammalian model for human neoplastic disease wherein histologically intact human neoplastic tissue is transplanted onto the corresponding organ of the model, said model being sufficiently immunodeficient to allow the transplanted tissue to grow and mimic the progression of neoplastic disease in the human donor.

In another aspect, the present invention provides a novel non-human mammalian model for human neoplastic disease wherein neoplastic tissue from a human organ is implanted in a vascularized matrix created on the corresponding organ of the immunodeficient model.

In a further aspect, the present invention provides a novel non-human mammalian model for human neoplastic disease wherein human neoplastic tissue is transplanted to the immunodeficient model by sandwiching the neoplastic tissue between an abdominal skin flap of the model and the corresponding organ of the model.

In yet another aspect, the present invention provides a novel non-human mammalian model for human neoplastic disease wherein neoplastic tissue from a human organ is transplanted to the immunodeficient model by securing, to the surface of the corresponding organ of the model, at least two pieces of neoplastic tissue in close proximity to each other.

In still another aspect, the invention provides a method of generating a non-human mammalian model for human neoplastic disease, the method comprising, providing a laboratory animal having sufficient immunodeficiency to allow implanted human neoplastic tissue to grow and mimic the progression of human neoplastic disease in the donor; by transplanting neoplastic tissue from a human organ into the corresponding organ of the immunodeficient animal.

In yet another aspect, the invention provides a method of generating a non-human mammalian model for human neoplastic disease, the method comprising, providing a laboratory animal having sufficient immunodeficiency to allow implanted human neoplastic tissue to grow and mimic the progression of neoplastic disease in the human donor, securing a vascularizing matrix to a selected organ of the animal and allowing the matrix to vascularize; and implanting neoplastic tissue from a human organ in the vascularized matrix wherein the matrix is located in the corresponding organ of the model.

In still another aspect, the invention provides a method of generating a non-human mammalian model for human neoplastic disease, the method comprising, providing a non-human mammalian laboratory animal having sufficient immunodeficiency to allow implanted human neoplastic tissue to grow and mimic the progression of neoplastic disease in the human donor; and sandwiching neoplastic tissue from a human organ between an abdominal skin flap created in the model and the Corresponding organ of the model.

In yet a further aspect, the invention provides a method of generating a non-human mammalian model from human neoplastic disease, the method comprising, providing a non-human mammalian laboratory animal having sufficient immunodeficiency to allow implanted human neoplastic tissue to grow and mimic the progression of neoplastic disease in the human donor; and securing at least two pieces of neoplastic tissue from a human organ to the surface of the corresponding organ of the model.

DETAILED DESCRIPTION OF THE INVENTION

Copending parent application, U.S. Ser. No. 253,990 filed Oct. 5, 1988, discloses animal models for human neoplastic disease wherein human neoplastic tissue is implanted into the corresponding organ of an immunodeficient animal that has sufficient immunodeficiency to allow the transplanted neoplastic tissue to grow and mimic the progression of neoplastic disease in the human donor. The method used to generate the animal models disclosed in U.S. Ser. No. 253,990 is described in the following paragraphs and in Examples I, II and III.

Animals that are suitable as immunodeficient hosts includes athymic rodents, i.e. rats and mice having no T-cell immunity. Particularly preferred animals are athymic mice which are readily available and may be obtained commercially from Charles River Laboratories, Inc., Wilmington, Mass. (Catalog identification: Crl:nu/nu(CD-1)BR, homozygous 28–42 days old).

The placement of neoplastic tissue in the immunodeficient host animal according to copending parent application, U.S. Ser. No. 253,990, is carried out by means of orthotopic implantation. This refers to an implant or graft transferred to a position formerly occupied by tissue of the same kind. The terminology orthotopic implantation is used to refer to the grafting of histologically intact human neoplastic tumor tissue from a human organ into the corresponding organ of an immunodeficient animal. Human neoplastic tissue that is utilized comprises tissue from fresh surgical specimens which are pathologically diagnosed tumors occurring in, for example, human kidney, liver, stomach, pancreas, colon, breast, prostate, lung, testis and brain. Such tumors include carcinomas as well as sarcomas and implantation thereof encompasses all stages, grades and types of tumors.

Prior to implantation, the human neoplastic tissue is maintained by placing it in a suitable nutrient medium, such as Eagle's Minimum Essential Medium containing ten percent fetal calf serum and a suitable antibiotic, such as gentamycin. The medium containing the tissue is then cooled to approximately 4° C. Tissue can be maintained in this manner for approximately twenty-four to seventy-two hours.

A selected tissue specimen is prepared for implantation by forming into a mass a suitable size for insertion into a suitably prepared cavity in the selected organ. The specimen size may vary from about 0.1×0.1×0.1 cm to about 0.2×0.1×0.1 cm. The technique used to form a specimen of suitable size comprises testing the tissue to size by pulling into pieces of the desired size with forceps or the like.

Microsurgical instruments typically used to carry out tissue implantation include a castrovijeo needle holder, jeweler's forceps (straight and curved), iris forceps, iris scissors and straight and curved tissue forceps, including one each with teeth and one each without teeth.

Prior to implantation of neoplastic tissue, the selected immunodeficient animal is anesthetized with a suitable anesthetic. Implantation of all organ tissue, except lung tissue, is conveniently accomplished by conventional anesthesia using ethyl ether. When lung tissue is implanted, pentabarbitol is used as the anesthetic.

Implantation of tissue from a hepatoma or tumor from a human liver is carried out utilizing the caudal lobe of the recipient animal's liver as the implantation site. Several loose sutures are placed over the lobe and an incision is made longitudinally under the liver serosa to accommodate a tumor mass of approximately 0.1×0.1×0.1 cm in size. After placement of the tumor mass in the incision, the sutures are pulled snugly over the tumor in order to secure it in place.

The process of implantation of tissue from a human pancreatic tumor is carried out by making an incision in the recipient animal's pancreas at the head of the organ near the duodenum. Care is exercised to select an a vascular area. An incision is made in the selected area and a tumor mass of approximately 0.1×0.1×0.1 cm is implanted in a manner identical to that described in the preceding paragraph. Tissue from all stages and all grades of pancreatic carcinoma may be implanted in this manner.

The implantation of tissue from a human mammary carcinoma is carried out by surgically implanting the tumor in the mammary fat pad of a recipient female animal. The tumor mass is approximately 0.1×0.1×0.1 cm in size. After placement of the tumor in the pocket, the pocket is closed with a suture. All stages and grades of mammary carcinoma may be implanted in this manner.

Implantation of tissue from a human prostatic carcinoma into the prostate of a recipient animal is carried out by surgically forming an opening in the prostate and then placing 5 tissue specimens of approximately 0.1×0.1×0.1 cm in size under the prostate capsule. After placement of the tissue specimen, the opening in the capsule is closed with appropriate sutures.

Implantation of tissue from a human testicular carcinoma into the testis of a recipient animal is carried out by penetrating the testis along the longitudinal axis with a number-18 gauge needle and injecting a tumor mass of approximately 0.1×0.1×0.1 cm in size through the needle. When the end of the tumor specimen is visible at the tip of the needle, the needle is gently withdrawn while visible tumor tissue is held in place with forceps. The holes made by the needle is then closed with a single suture.

In preparation for implantation of neoplastic lung tissue into the lungs of the recipient animal, a tracheotomy is performed and plastic tubing is incubated. Thereafter, implantation may be effected by several procedures. In one implantation procedure, tracheotomy tubing is advanced to reach either lung lobe(s); a small (0.1×0.1×0.1 cm) tumor mass is injected through the tubing; and the tubing is then removed and the tracheal wound is closed with a suture.

In the other implantation procedure, precautionary tubing is inserted into the trachea; a small stab wound is made on the right chest to bring up a lobe of the right lung which plugs the thoracic cavity thereby preventing collapse of the lung; the lung lobe is gently clamped at the base and two ligatures are loosely placed on the lung; an incision is made on the lung, a tumor mass of approximately 0.1×0.1×0.1 cm is imbedded therein; the ligatures are snugly tied; and the lung lobe is placed back into the thoracic cavity and the wound is closed. Tissue-from all stages and grades of small cell and non-small cell lung carcinomas may be implanted by either of the foregoing procedures.

In order to implant neoplastic human brain tissue into the recipient animal's brain, a bur hole is made through the parietal cranial bone of the animal. A tumor mass of approximately 0.1×0.1×0.1 cm is selected and implanted in the brain. The hole in the cranial bone is then sealed by means of bone wax.

The present invention is an extension and improvement of the invention disclosed in copending parent application U.S. Ser. No. 253,990 filed Oct. 5, 1988. In the present invention, a non-human mammalian model for human neoplastic disease is generated by improved methods of transplanting histologically intact neoplastic tissue from a human organ to the corresponding organ of an immunodeficient model that has sufficient immunodeficiency to allow the transplanted tissue to grow and mimic the progression of neoplastic disease in the human donor. The methods used to generate the animal models of the present invention are described in the following paragraphs and in Examples IV–VII.

Transplantation of neoplastic tissue from a human organ to the corresponding organ of an immunodeficient animal as taught in the present invention is referred to as orthotopic transplantation. In the present invention, the terminology orthotopic transplantation is used to refer to the grafting of histologically intact human neoplastic tumor tissue from a human organ onto the corresponding organ of an immunodeficient animal.

Human neoplastic tissue can be utilized in the present invention as well as preparation of such tissue has been described earlier in accordance with copending parent application U.S. Ser. No. 253,990.

One preferred method for transplanting human neoplastic tissue to an immunodeficient animal model according to the present invention utilizes a vascularizing matrix. The purpose of the matrix is to induce the development of blood vessels and thereby enhance the survival and growth of the transplanted neoplastic tissue. In this method, the matrix is transplanted on the appropriate organ by means of a surgical suture(s). When the matrix becomes well vascularized, which usually occurs in about twenty (20) days, the histologically intact specimen of human neoplastic tissue is implanted directly into the vascularized matrix. The term vascularizing matrix as used herein refers to liquid-permeable, water-insoluble material having the general physical characteristics of a sponge and being substantially absorbable in a living mammalian body. Specific examples of such materials are absorbable gelatin sponge and cellulose sponge. While absorbable gelatin sponge is the preferred vascularizing matrix, those skilled in the art will realize that a number of materials can be utilized as the vascularizing matrix.

Another preferred method of transplanting human neoplastic tissue according to the present invention utilizes an internal skin flap over the transplanted surgical specimen. Use of the skin flap induces vascularization and take of the transplanted tissue. In this method, a U shaped incision is made in the abdomen of the immunodeficient animal model and the resulting skin flap is lifted up and the abdominal wall is opened along the line alba. The cecum (or other organ) is accessed through the abdominal incision, and neoplastic tissue is placed between the cecum serosa (or other organ) and the skin flap. Surgical sutures are applied along the edge of the skin flap to fix the flap to the cecum (or other organ). The cecum (or other organ) together with the skin flap is put back into the abdominal cavity and peritoneum and rectus muscles are closed with sutures. Finally, the skin layer is also closed with sutures and surgical adhesive is applied to ensure a good closure of the abdominal wall.

Still another preferred method of transplanting human neoplastic tissue to an immunodeficient animal model according to the present invention utilizes multiple pieces of tissue arranged in a shish-kabob configuration. In this method, a thread-like material is passed through at least two pieces of human neoplastic tissue and the resulting tissue arrangement is positioned on the surface of the corresponding organ of the immunodeficient mode. The shish-kabob configuration is attached to the animal organ by securing a pair of terminal ends of the thread-like material to the organ. The term thread-like material as used herein refers to absorbable surgical suture such as, for example, Chromic Gut surgical suture and Coated VicrylR surgical suture, both obtainable from Ethicon, Inc. located in Somerville, N.J. A particularly preferred variation of this method of transplantation comprises interspersing pieces of normal tissue between pieces of neoplastic tissue in the shish-kabob configuration.

The animal models of the present invention are particularly useful in studying the progression of human neoplastic disease. These studies, in combination with other clinical testing modalities such as diagnostic imaging, help in the selection of the most appropriate form of treatment.

For example, when an animal model of the present invention is subjected to tumor imaging, the clinician is allowed to identify both primary and secondary sites of tumor growth and to estimate the overall burden of the tumor on the animal. Tumor imaging is conventionally carried out by injecting the animal model with a labeled anti-tumor antibody such as an antibody labeled with a radioactive isotope; allowing the antibody time to localize within the tumor; and then scanning the animal using a radiation detector. When a computer is used to compile an image of the radioactivity detected in the animal's body, the computer can color code the image according to the intensity of the radiation. Zones of high radioactivity in regions of the body not expected to accumulate the antibody or its metabolites indicate the possible present invention.

The animal models of the present invention can also be used to screen new anti-neoplastic agents to determine the ability to such agents to affect tumors at the primary site and also at distant metastatic sites or to prevent distant metastases from occurring. The models will be also useful for individualized chemosensitivity testing of a cancer patient's tumors.

Additionally, the animal models of the present invention are useful in studying the effects of nutrition on the progression of human neoplastic disease. These studies can be particularly significant in view of the demonstrated impact of various deficiencies on healthy subjects.

Examples I–III illustrate the invention which is set forth in copending application U.S. Ser. No. 253,990, filed Oct. 5, 1988. Examples IV–X are provided in order to illustrate the present invention and are not be construed as limiting the scope of the invention or as being inclusive of all embodiments of the invention.

EXAMPLE I

In this example, fresh surgical specimens of tissue from a tumor excised from a human kidney were transplanted into the kidneys of nude mice. The tissue specimens, which were pathologically diagnosed as renal cell carcinoma, were prepared to size by the teasing procedure described earlier.

Five athymic nude mice age four (4) to six (6) weeks were selected as the animal recipients for the implants. In preparation for surgery, the mice were anesthetized with ether. An incision was made in each animal to access the kidney under the capsule. A wedge shaped cavity was formed by excision of the renal cortex of each recipient kidney and a mass of tumor tissue of approximately 0.1×0.1×0.1 cm was placed under the renal capsule. A suture was then employed to secure the implant in place.

The five mice of this example were still alive six months later. Approximately one month following implantation of the tissue, the mice were surgically opened and the implanted tumors were observed. In each case, the tumor was found to have taken, i.e. the implanted neoplastic tissue had invaded adjacent tissue. Histological analysis was performed on the tissue implants at this time. Such analysis comprised removing tissue samples from each animal and comparing the samples with a tissue sample from the tissue donor.

Preparation of the tissue samples for histological analysis was carried out by (1) fixing the sample in formalin; (2) embedding the fixed sample in paraffin; (3) preparing 5-micron sections of the fixed, embedded sample; (4) staining the sections with hematoxylin and cosin; and (5) microscopically observing the tissue structure in each section.

Histological analysis revealed that the tissue in the recipient animals preserved its architecture and tissue type and mimicked progression of the disease in the human donor.

EXAMPLE II

In this example, specimens of human tissue excised from the stomach and pathologically diagnosed as gastric carcinoma were prepared to size by the teasing procedure described earlier.

Five athymic nude mice age four (4) to six (6) weeks were selected as the animal recipients for the implants. In preparation for surgery, the mice were anesthetized with ether.

Each anesthetized mouse was opened to provide access to the stomach. An incision was made in the stomach wall using a number 11 scalpel taking care to penetrate the mucosal layer. A pocket was formed large enough to receive five tumor masses of about 0.1×0.1×0.1 cm each. A tumor piece of approximately this size was selected and inserted into the pocket and the incision was cloned using a 7-0 suture.

The five mice of this example have survived for about three (3) to four (4) months and otherwise appear healthy. Subsequent surgical opening of the stomach of these mice has verified that the tumors have taken.

EXAMPLE III

In this example, specimens of human tissue removed from a human colon and pathologically diagnosed as colon carcinoma were prepared to size by the testing procedure described earlier.

Five athymic nude mice, age four (4) to six (6) weeks were selected as the animal recipients for the implants. In preparation for surgery, the mice were anesthetized with ether. Each anesthetized mouse was opened to provide access to the colon. A pocket or cavity was surgically formed in the seromuscular layer with care exercised not to enter the lumen. Five to ten tumor masses of approximately 0.1×0.1×0.1 cm each were inserted into the pocket which was then closed with a suture.

Four of the five mice which underwent this implant surgery have survived for three to four months and appear to be in a good health. Approximately one month following tissue implantation, the mice were surgically opened and the tumors were observed to have taken.

EXAMPLE IV

This example relates to the use of a vascularizing matrix to induce vascularization and take of orthotopically transplanted human tumor tissue.

A surgical tissue specimen, removed from a human colon and pathologically diagnosed as colon carcinoma, was washed with colon-wash medium. Necrotic tissue was removed and the tumor was then cut into small pieces (about 1-$mm^3$). Colon-wash medium, used to remove infectious intestinal material, was formulated by combining 500 ml of Minimum Essential Medium with Earle's salts (MEM Earle's) with 70 ml fetal bovine serum, 75.2 mg Penicillin G sodium salt, 125 mg Streptomycin, 10 ml Fungizone antibiotic (250 ug amphotericin B and 205 ug sodium deoxycholate/ml in deionized distilled water), 5 mg Tetracycline, 50 mg Amikacin, 75 mg chloramphenicol and 50 mg Gentamycin.

GelfoamR brand of absorbable, sterile gelatin sponge (obtained from The Upjohn Co., Kalamazoo, Mich.) was hydrated with MEM Earle's. The hydrated sponge was cut into approximately 0.3–0.5×0.3–0.5×0.3–0.5 cm pieces which were transplanted onto the cecum of nude mice by means of a simple surgical suture on top of the cecum serosa. After 20 days, the sponges became well vascularized.

The transplanted vascularized sponges were cut in the center to make a pocket and about 10–15 of the previously prepared 1-$mm^3$ tumor pieces were implanted into each pocket which was closed by means of a surgical suture. The tumor grew locally and regional as well as liver metastases occurred.

EXAMPLE V

This example relates to the use of an internal skin flap to induce vascularization and take of orthotopically implanted human tumor tissue.

The tumor tissue used is identical to tissue used in Example IV and was prepared for implantation according to the procedure described in Example IV.

Skin flaps were constructed in the lower abdomen of nude mice by making incisions along three sides of a rectangular area (a U-shaped incision). The flap was lifted up and the abdominal wall was opened along the line alba. The cecum was exteriorized from the abdominal cavity and tumor pieces (about 1-$mm^3$) were placed between the cecum serosa and the skin flap. Surgical sutures were applied along the two opposing edges of the flap to fix the flap on the cecum. The cecum, together with the skin flap was put back into the abdominal cavity. Peritonerum and rectus muscles were closed with sutures followed by reattachment of the skin flap with sutures. As a last step, surgical adhesive was applied to ensure good closure of the abdominal wall. The tumor grew at the implanted site and formed abdominal metastases.

EXAMPLE VI

This example relates to the use of a shish-kabob tissue configuration to effect orthotopic transplantation of human tumor tissue.

A surgical tissue specimen, removed from a human colon and pathologically diagnosed as colon carcinoma, was well washed with colon-wash medium. Necrotic tissue was removed and the tumor was then cut into small 1-$mm^3$ pieces. Eight of the 1-$mm^3$ pieces were assembled in a shish-kabob configuration by stringing the pieces together on a piece of surgical suture.

The shish-kabob tissue configuration was transplanted in nude mice by placement of the configuration on the mouse colon approximately 0.5 to 1 cm away from (i.e., up-stream of) the animals cecum. The configuration is held in place by securing the terminal ends of the suture material to the organ of the animal.

EXAMPLE VII

As shown below, local growth, regional metastasis, and in some instances, distant organ metastasis have been achieved using the three novel methods of orthotopic transplantation described in the present invention.

TABLE 1

Orthotopic Transplantation of Human Colon Carcinoma to the Colon of Nude Mice

| Method | Number of Animals | Local Growth | Regional Metastasis | Distant Metastasis |
|---|---|---|---|---|
| Matrix | 3 | 56–62 days | 56–62 days | 160 days |
| Skin Flap | 3 | 48–62 days | 48–62 days | |
| Shish-kabob | 4 | 62–138 days | 62–138 days | |

EXAMPLE VIII

This example relates to the use of surgical adhesive to glue a piece of tumor tissue onto the top of the urinary bladder of the nude mouse.

A piece of tumor tissue specimen about 2-$mm^3$ size was prepared for tumor transplantation. The nude mouse was operated on under surgical anesthesia with the full exposure of the urinary bladder. A small amount of surgical adhesive (2-cyanoacrylic acid ester) was applied on the top of the urinary bladder and the previously prepared tumor piece was then glued onto the top of the urinary bladder. The abdomen was closed with surgical sutures.

Using the transplantation method described above, we transplanted the ras-transfected human bladder RT-10 carcinoma cell line xenograft. As a result, we achieved unexpected extensive growth and metastases, including invasion of the whole thickness of the urinary bladder wall, lymph node metastases, and multi-organ metastases in the liver, pancreas, spleen, ovary, kidney, ureter and lung. This transplantation result of RT-10 is in striking contrast to the result obtained when RT-10 was injected transurethrally as disaggregated cells where only local invasion and no distant metastasis were observed. (Theodorescu et al., Proc. Natl. Acad. Sci(1990), Vol 87, 9047–9051.)

EXAMPLE IX

In this example, a human tongue cancer specimen, which was prepared by being cut into 1-$mm^3$ pieces, was transplanted orthotopically to the floor of the mouth of a nude mouse.

An incision was made along the midline on the upper neck of the mouse. After blunt dissection of the muscles of the floor of the mouth, five pieces of prepared tumor tissue were implanted in between the muscles deep in the floor of the mouth. Surgical sutures were applied to close the dissected muscles and skin layer.

Extremely invasive growth was observed which involved the whole jaw as well as deep in the nasopharynx. This is distinctly different form growth observed when tumor pieces were implanted subcutaneously in the neck area. The subcutaneously grown tumor was completely encapsulated and exhibited no invasion of the adjacent tissue.

EXAMPLE X

In this example, a human pancreatic tumor specimen was prepared by being cut into 1-$mm^3$ pieces, and tumor pieces were transplanted onto the nude mouse pancreas.

A midline incision was made on the upper abdomen of the nude mouse muscle layers and the peritoneum were opened along the line alba. Ten (10) pieces of previously prepared tumor pieces were assembled in a shish-kebab configuration by striking the pieces together on a piece of surgical suture. The configuration was secured on the pancreas. The abdomen was then closed with one layer surgical suture.

Two different kinds of human pancreatic cell line xenografts were transplanted as described above. Invasive growth was observed into both cases, including the invasion of the duodenum and spleen.

Although the foregoing invention has been described in some detail by way of illustration and example for purposes of clarity of understanding, it will be obvious that certain changes and modifications may be practiced within the scope of the appended claims.

What is claimed is:

1. A nude mouse model for *progression of* human neoplastic disease, *the progression of said disease being characterized by growth of a primary tumor site and metastasis to secondary tumor sites,* wherein said mouse [is characterized by having] *has* histologically intact human neoplastic tissue of at least 1 $mm^3$ in size transplanted onto an organ of said mouse which corresponds to the human organ from which said tissue is originally obtained; and

[having] *has* sufficient immuno-deficiency to allow said transplanted neoplastic tissue to grow [and] *at said primary site and metastasize to said secondary tumor sites, so as to* mimic the progression of the neoplastic disease *including the metastatic behavior of said neoplastic disease* in [the human donor] *humans*.

2. A nude mouse model according to claim 1 wherein said neoplastic tissue is selected from breast tissue, ovarian tissue [or] *and* pleural tissue.

3. A nude mouse model according to claim 2 wherein said neoplastic tissue is obtained from human breast tissue.

4. A nude mouse model according to claim 3 wherein said human neoplastic breast tissue is implanted in the mammary fat pad of the mouse.

5. A nude mouse model according to claim 2 wherein said neoplastic tissue is obtained from human ovarian tissue.

6. A nude mouse model according to claim 5 wherein said human neoplastic ovarian tissue is implanted in the ovarian capsule of the mouse.

7. A nude mouse model according to claim 5 wherein said human neoplastic ovarian tissue is transplanted by securing to the surface of the mouse ovary at least two pieces of neoplastic tissue in close proximity to each other.

8. A nude mouse model according to claim 2 wherein said neoplastic tissue is obtained from human pleural tissue.

9. A nude mouse model according to claim 8 wherein said neoplastic tissue is implanted in the parietal pleura of the mouse.

10. A nude mouse model according to claim 9 wherein said neoplastic tissue is implanted in the visceral pleura of the mouse.

11. A method of generating a nude mouse model for *progression of* human neoplastic disease, *the progression of said disease being characterized by growth of a primary tumor site and metastasis to secondary tumor sites,* said method comprising:

transplanting histologically intact human neoplastic tissue of at least 1 $mm^3$ in size [transplanted] onto an organ of a nude mouse which corresponds to the human organ from which said tissue is originally obtained; and allowing said transplanted tissue to grow [and] *at said primary site and metastasize to said secondary tumor sites, so as to* mimic progression of the neoplastic disease *including the metastatic behavior of said neoplastic disease* in [the human donor] *humans*.

12. A method of generating a nude mouse according to claim 11 wherein said human neoplastic tissue is selected from breast tissue, ovarian tissue [or] *and* pleural tissue.

*13. A nude rodent model for progression of human neoplastic disease, the progression of said disease being characterized by growth of a primary tumor site and metastasis to secondary tumor sites, wherein said rodent has histologically intact human neoplastic tissue of at least 1 $mm^3$ in size transplanted onto an organ of said rodent which corresponds to the human organ from which said tissue is originally obtained; and*

*has sufficient immuno-deficiency to allow said transplanted neoplastic tissue to grow at said primary site and metastasize to said secondary tumor sites, so as to mimic the progression of the neoplastic disease including the metastatic behavior of said neoplastic disease in humans.*

*14. The nude rodent model for human neoplastic disease of claim 13, wherein said rodent is a rat.*

*15. An immunodeficient rodent model for progression of human neoplastic disease, the progression of said disease being characterized by growth of a primary tumor site and metastasis to secondary tumor sites, wherein said rodent has histologically intact human neoplastic tissue of at least 1 $mm^3$ in size transplanted onto an organ of said rodent which corresponds to the human organ from which said tissue is originally obtained; and*

*has sufficient immuno-deficiency to allow said transplanted neoplastic tissue to grow at said primary site and metastasize to said secondary tumor sites, so as to mimic the progression of the neoplastic disease including the metastatic behavior of said neoplastic disease in humans.*

*16. The immunodeficient rodent model for human neoplastic disease of claim 15, wherein said rodent is a rat.*

*17. The immunodeficient rodent model for human neoplastic disease of claim 15, wherein said rodent is a mouse.*

*18. The immunodeficient rodent model for human neoplastic disease of claim 17, wherein said rodent is a severe combined immunodeficient (SCID) mouse.*

*19. A method of generating a nude rodent model for progression of human neoplastic disease, the progression of said disease being characterized by growth of a primary tumor site and metastasis to a secondary tumor sites, said method comprising:*

*transplanting histologically intact human neoplastic tissue of at least 1 $mm^3$ in size onto an organ of a nude rodent which corresponds to the human organ from which said tissue is originally obtained; and*

*allowing said transplanted tissue to grow at said primary site and metastasize to said secondary tumor sites, so as to mimic progression of the neoplastic disease including the metastatic behavior of said neoplastic disease in humans.*

*20. The method of generating a nude rodent model for human neoplastic disease of claim 19, wherein said rodent is a rat.*

*21. A method of generating an immunodeficient rodent model for progression of human neoplastic disease, the progression of said disease being characterized by growth of a primary tumor site and metastasis to secondary tumor sites, said method comprising:*

*transplanting histologically intact human neoplastic tissue of at least 1 $mm^3$ in size onto an organ of an immunodeficient rodent which corresponds to the human organ from which said tissue is originally obtained; and*

*allowing said transplanted tissue to grow at said primary site and metastasize to said secondary tumor sites, so as to mimic progression of the neoplastic disease including the metastatic behavior of said neoplastic disease in humans.*

*22. The method of generating an immunodeficient rodent model for human neoplastic disease of claim 21, wherein said rodent is a rat.*

*23. The method of generating an immunodeficient rodent model for human neoplastic disease of claim 21, wherein said rodent is a mouse.*

*24. The method of generating an immunodeficient rodent model for human neoplastic disease of claim 23, wherein said rodent is a severe combined immunodeficient (SCID) mouse.*

*25. A nude rodent model for progression of human neoplastic disease, the progression of said disease being characterized by growth of a primary tumor site and metastasis to secondary tumor sites, wherein said rodent has histologically intact human neoplastic tissue transplanted onto an organ of said rodent which corresponds to the human organ from which said tissue is originally obtained; and*

*has sufficient immuno-deficiency to allow said transplanted neoplastic tissue to grow at said primary site and metastasize to said secondary tumor sites, so as to mimic the progression of the neoplastic disease including the metastatic behavior of said neoplastic disease in humans.*

*26. An immunodeficient rodent model for progression of human neoplastic disease, the progression of said disease being characterized by growth of a primary tumor site and metastasis to secondary tumor sites, wherein said rodent has histologically intact human neoplastic tissue transplanted onto an organ of said rodent which corresponds to the human organ from which said tissue is originally obtained; and*

*has sufficient immuno-deficiency to allow said transplanted neoplastic tissue to grow at said primary site and metastasize to said secondary tumor sites, so as to mimic the progression of the neoplastic disease including the metastatic behavior of said neoplastic disease in humans.*

*27. A nude rodent model according to claim 13 wherein said neoplastic tissue is selected from breast tissue, ovarian tissue or pleural tissue.*

*28. A nude rodent model according to claim 27 wherein said neoplastic tissue is obtained from human breast tissue.*

*29. A nude rodent model according to claim 27 wherein said neoplastic tissue is obtained from human ovarian tissue.*

*30. A nude rodent model according to claim 27 wherein said neoplastic tissue is obtained from human pleural tissue.*

*31. An immunodeficient rodent model according to claim 15 wherein said neoplastic tissue is selected from breast tissue, ovarian tissue or pleural tissue.*

*32. An immunodeficient rodent model according to claim 31 wherein said neoplastic tissue is obtained from human breast cancer.*

*33. An immunodeficient rodent model according to claim 31 wherein said neoplastic tissue is obtained from human ovarian tissue.*

*34. An immunodeficient rodent model according to claim 31 wherein said neoplastic tissue is obtained from human pleural tissue.*

*35. The method according to claim 19 wherein said neoplastic tissue is selected from breast tissue, ovarian tissue or pleural tissue.*

*36. The method according to claim 35 wherein said neoplastic tissue is obtained from human breast tissue.*

*37. The method according to claim 35 wherein said neoplastic tissue is obtained from human ovarian tissue.*

*38. The method according to claim 35 wherein said neoplastic tissue is obtained from human pleural tissue.*

*39. The method according to claim 21 wherein said neoplastic tissue is selected from breast tissue, ovarian tissue or pleural tissue.*

*40. The method according to claim 39 wherein said neoplastic tissue is obtained from human breast tissue.*

*41. The method according to claim 39 wherein said neoplastic tissue is obtained from human ovarian tissue.*

*42. The method according to claim 39 wherein said neoplastic tissue is obtained from human pleural tissue.*

*43. A nude rodent model according to claim 25 wherein said neoplastic tissue is selected from breast tissue, ovarian tissue or pleural tissue.*

*44. A nude rodent model according to claim 43 wherein said neoplastic tissue is obtained from human breast tissue.*

*45. A nude rodent model according to claim 43 wherein said neoplastic tissue is obtained from human ovarian tissue.*

*46. A nude rodent model according to claim 43 wherein said neoplastic tissue is obtained from human pleural tissue.*

*47. An immunodeficient rodent model according to claim 26 wherein said neoplastic tissue is selected from breast tissue, ovarian tissue or pleural tissue.*

*48. An immunodeficient rodent model according to claim 47 wherein said neoplastic tissue is obtained from human breast tissue.*

*49. An immunodeficient rodent model according to claim 47 wherein said neoplastic tissue is obtained from human ovarian tissue.*

*50. An immunodeficient rodent model according to claim 47 wherein said neoplastic tissue is obtained from human pleural tissue.*

* * * * *